(12) United States Patent
Sarofim et al.

(10) Patent No.: US 9,316,656 B2
(45) Date of Patent: Apr. 19, 2016

(54) LID SEPARATION DEVICE AND METHODS

(75) Inventors: Emad Sarofim, Hagendorn (CH); Lotar Schenk, Knonau (CH); Hans-Peter Wahl, Huenenberg (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 662 days.

(21) Appl. No.: 12/617,611

(22) Filed: Nov. 12, 2009

(65) Prior Publication Data

US 2010/0120599 A1 May 13, 2010

(30) Foreign Application Priority Data

Nov. 12, 2008 (EP) .................................. 08105781

(51) Int. Cl.
| | |
|---|---|
| *B01L 3/00* | (2006.01) |
| *G01N 35/04* | (2006.01) |
| *G01N 21/03* | (2006.01) |
| *G01N 21/07* | (2006.01) |
| *G01N 21/25* | (2006.01) |

(52) U.S. Cl.
CPC .............. *G01N 35/04* (2013.01); *B01L 3/5025* (2013.01); *G01N 21/03* (2013.01); *G01N 21/07* (2013.01); *G01N 21/253* (2013.01); *B01L 2200/026* (2013.01); *B01L 2300/048* (2013.01); *B01L 2300/069* (2013.01); *B01L 2300/0829* (2013.01); *B01L 2300/0858* (2013.01); *B01L 2400/0409* (2013.01); *G01N 2021/0328* (2013.01); *G01N 2035/0449* (2013.01)

(58) Field of Classification Search
CPC ................ B01L 3/5021; B01L 3/5025; B01L 2300/0829; B01L 2300/858; B01L 2400/0409; G01N 21/07
USPC ................... 422/527, 73, 547, 548, 551, 552; 436/177, 180
See application file for complete search history.

(56) References Cited

U.S. PATENT DOCUMENTS

| | | | |
|---|---|---|---|
| 5,084,240 A | 1/1992 | Babson | |
| 5,256,376 A * | 10/1993 | Callan et al. ..................... | 422/72 |
| 5,605,529 A | 2/1997 | Petithory | |
| 6,450,203 B1 * | 9/2002 | Backhouse et al. ........... | 137/807 |
| 6,485,690 B1 * | 11/2002 | Pfost et al. ..................... | 422/552 |
| 7,141,416 B2 * | 11/2006 | Krutzik ....................... | 435/288.5 |
| 2005/0136546 A1 * | 6/2005 | Berndt et al. .................. | 436/45 |
| 2006/0177352 A1 | 8/2006 | Ziegmann et al. | |
| 2008/0025873 A1 * | 1/2008 | Harding ......................... | 422/72 |

FOREIGN PATENT DOCUMENTS

| | | |
|---|---|---|
| EP | 0791394 A2 | 8/1997 |
| EP | 0791394 A3 | 7/1998 |
| EP | 1547686 A1 | 6/2005 |
| EP | 1547691 A1 | 6/2005 |
| JP | 04348250 A | 12/1992 |

(Continued)

*Primary Examiner* — Jill Warden
*Assistant Examiner* — Dwayne K Handy
(74) *Attorney, Agent, or Firm* — M. Reza Savari

(57) ABSTRACT

The present invention includes a device comprising a lid and a vessel forming an interface that allows transfer of waste from a purification chamber to a waste chamber and method for purification of an analyte are disclosed wherein a supernatant is separated from a solid phase to which an analyte is bound by centrifugation via the lid of the device. The present invention also includes methods for use of the device.

14 Claims, 9 Drawing Sheets

(56) References Cited

FOREIGN PATENT DOCUMENTS

| | | | |
|---|---|---|---|
| JP | 1993302930 | A | 11/1993 |
| JP | 0650968 | A | 2/1994 |
| WO | 9303347 | A1 | 2/1993 |
| WO | 9310455 | A1 | 5/1993 |
| WO | 9400762 | A1 | 1/1994 |
| WO | 9925470 | A1 | 5/1999 |
| WO | 2004004886 | A2 | 1/2004 |
| WO | 2004004886 | A3 | 1/2004 |

\* cited by examiner

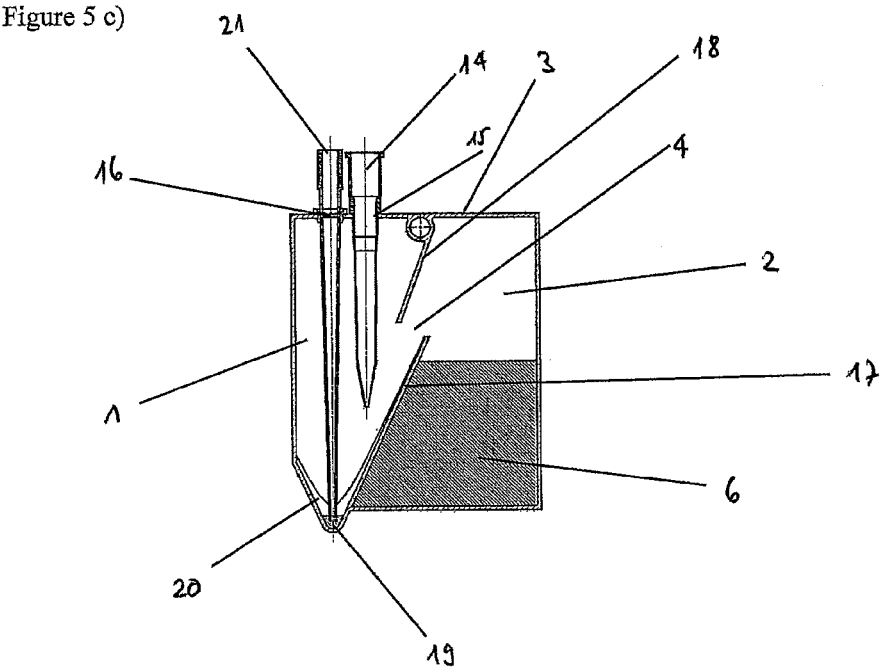

Fig 7
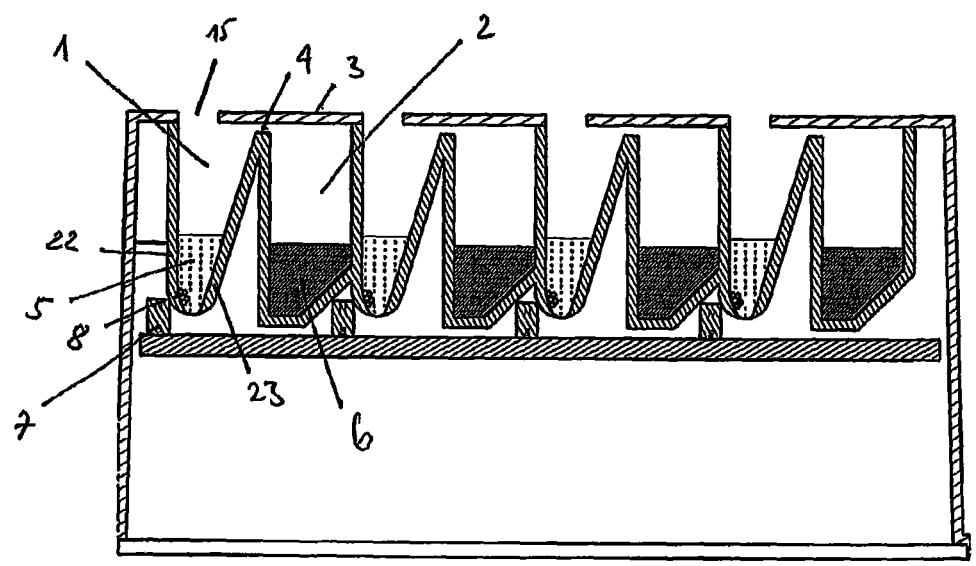
a)
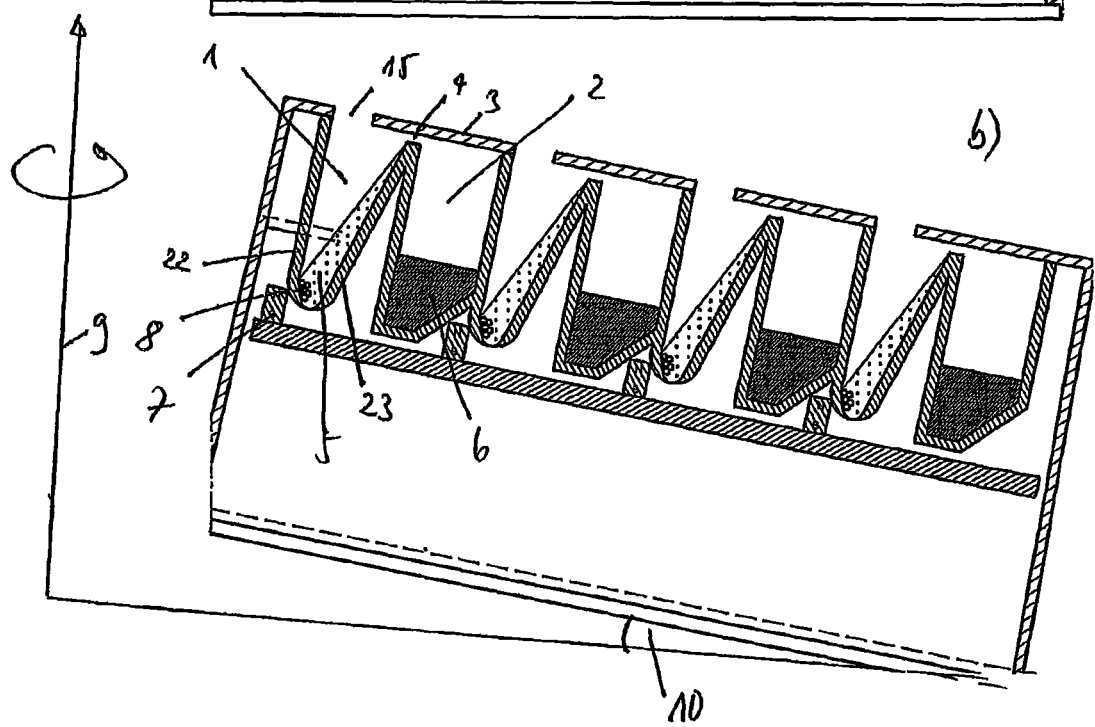
b)

LID SEPARATION DEVICE AND METHODS

RELATED APPLICATIONS

The present application claims the benefit of European Patent Application 08105781.2 filed Nov. 12, 2008, the entire contents of which is hereby incorporated herein by reference in its entirety.

FIELD OF THE INVENTION

The present invention relates to a separation device, a separation method and analytical and sample preparation systems for separating a supernatant from a solid phase.

Separation, purification or concentration, for example of an analyte present in a biological sample are important steps of analytical methods. Such analytical methods employ analytical systems to separate and purify analytes from biological samples. Separation and purification commonly consists of binding the analyte to a solid support, either specifically using antigen-specific antibodies or sequence specific complementary oligonucleotide probes immobilized on a solid support; or non-specifically. The analyte is bound to the solid support. Other material present in the biological sample is removed by subsequent washing steps. Commonly, multiple washing steps are used. For each washing step, a washing solution is added to the solid support with bound analyte, the solid support is sequestered and the remaining liquid, forming a supernatant, is removed. After the final wash, the remaining liquid has to be removed and subsequently, the analyte may be eluted from the solid support. Addition and removal of solutions is commonly preformed using pipettors with pipette tip and/or cannules which form part of sample preparation and/or analytical systems. Immobilization, washing and elution are commonly performed in multiwell plates or sample tubes capable of holding liquids.

DESCRIPTION OF THE INVENTION

The present invention relates to a separation device for separating a supernatant from a solid phase, comprising
  (i) a vessel for holding one or more liquids comprising one or more analytes and a solid phase to which said one or more analytes can be bound, said vessel comprising
    a) at least one purification chamber holding one of said liquids and said solid phase, wherein one or more of said analytes is bound to said solid phase within said purification chamber
    b) at least one waste chamber to which the liquid can be transferred following binding of said analyte or analytes to the solid phase, and
  (ii) a lid covering said vessel.

The interface between said vessel and said lid is dimensioned to allow the liquid to transfer from the purification chamber holding the solid phase to said waste chamber when exposed to centrifugal force after said analyte or analytes is bound to said solid phase, while the solid phase remains in said purification chamber. Preferably, the liquid is an aqueous solution.

The term "interface" as used herein is meant to relate to the area of interaction between the lid, the purification chamber and the waste chamber. Preferred embodiments of said interface are described hereinafter.

The separation device as described herein allows for efficient separation of a bound analyte or of a precipitate comprising an analyte or of an analyte bound covalently or non-covalently to the walls of the purification chamber from the remaining liquid. This efficient separation permits to reduce the number of wash steps and other processing steps and, thus, reduces the time for the preparation and purification of the analyte comprised in the solid phase. It also reduces the risk of cross-contaminations between the purification chambers within one device and/or of contaminations of the environment by said liquids.

The term "supernatant" as used herein relates to any fluid which has to be separated from a solid phase.

The term "solid phase" as used herein relates to any solid phase that comprises an analyte either by forming a precipitate with the analyte or by binding the analyte. A preferred embodiment of said solid phase are magnetic particles. A magnetic particle is a particle made of a material which can be attracted by a magnet, i.e. ferromagnetic or superparamagnetic materials. The invention prefers in particular ferromagnetic particles. Magnetide ($Fe_3O_4$) or $Fe_2O_3$ are particularly preferred. A magnetic particle is, however, also understood to include materials which contain (smaller) magnetic particles. This includes in particular Iriodin 600 a pigment which is commercially available from Merck (Darmstadt, Germany). The invention prefers in particular particles with an average grain size of less than 100 μm. A particularly preferred grain size ranges between 10 and 60 μm. The preferred grain distribution is relatively homogeneous; in particular, there are almost no particles smaller than 10 μm or larger than 60 μm. Particles which satisfy this requirement are described for example in WO 90/06045.

The term "analyte" is understood to be any molecule, or aggregate of molecules, including a cell or a cellular component of a virus, found in a sample. Thus, as a non-limiting example, an analyte may be a nucleic acid of interest or a protein of interest which is investigated and its presence or absence, or its concentration in a biological sample is determined as its presence or absence is indicative of a certain condition or disease of a human or animal. Further included in the scope of the term "analyte" are fragments of any such molecule found in a sample. In one preferred embodiment, said analyte is a biological analyte, more preferably a nucleic acid. Said nucleic acid may be RNA or DNA or any derivative thereof. In a more preferred example, said analyte is a virus, more preferably the hepatitis A virus (HAV), hepatitis B virus (HBV), hepatitis C virus (HCV), the human immunodeficiency virus (HIV), the human papilloma virus (HPV), parvovirus B19, CT/NG. The analyte may also, in a more preferred example, be a bacteria such as MAI or MTB.

The term "liquid" as used herein relates to any fluid comprising an analyte. Non-limiting examples of said liquid are biological samples, such as blood, plasma or serum, urine, brain fluids etc. The term "liquid" may also relate to solutions which comprise an analyte following lysis of a biological sample, such as a tissue sample.

Commonly, in the field of Molecular Diagnostics, amplification of analyte is used for determining the amount of analyte in sample, and the amount is then correlated with a disease state. Such amplification methods include the polymerase chain reaction (PCR). The amplification method may also be the Ligase Chain Reaction (LCR, Wu and Wallace, Genomics 4 (1989)560-569 and Barany, Proc. Natl. Acad. Sci. USA 88 (1991)189-193); Polymerase Ligase Chain Reaction (Barany, PCR Methods and Applic. 1 (1991)5-16); Gap-LCR (PCT Patent Publication No. WO 90/01069); Repair Chain Reaction (European Patent Publication No. EP 439,182 A2), 3SR (Kwoh, et al., Proc. Natl. Acad. I Sci. USA 86 (1989)1173-1177; Guatelli, et al., Proc. Natl. Acad. Sci. USA 87 (1990)1874-1878; PCT Patent Publication No. WO 92/0880A), and NASBA (U.S. Pat. No. 5,130,238). Further, there are strand displacement amplification (SDA), transcription mediated amplification (TMA), and Q0-amplification (for a review see e.g. Whelen and Persing, Annul Rev. Microbiol. 50 (1996) 349-373; Abramson and Myers, Current Opinion in Biotechnology 4 (1993)41-47).

The use of the present invention is not only of interest in Molecular Diagnostics, but is also useful for Immunoassays. Such assays are well known in the art.

In one preferred embodiment, said separation device comprises a vessel which is a multiwell plate. Thus, with the invention described herein, multiple samples can be processed efficiently in parallel. Said multiwell plate comprises at least two purification chambers.

One advantage of the preferred embodiment disclosed herein is that by using existing formats of multiwell plates and lids, it is possible to use tools for producing them which are already existing for the production of commonly used multiwell plates and lids.

The vessel can be designed to comprise an equal number of purification chambers and waste chambers. In one preferred embodiment of such a design, said vessel comprises 48 purification chambers and 48 waste chambers. However, other sizes, including multiples of the numbers exemplified hereinbefore, can be envisioned.

Another preferred design of the separation device comprises less waste chambers than purification chambers. In one preferred embodiment, only one waste chamber is comprised in the separation device. This requires that all purification chambers are fluidically connected to said one waste chamber. One possible embodiment of such fluidic connection are fluidic channels to which all of the purification chambers are connected, wherein said channels are connected to the waste chamber. In another preferred embodiment, more than one waste chamber, but still less waste chambers that purification chambers are comprised in said separation device. In a more preferred embodiment, the separation device comprises one waste chamber per row of purification chambers. Thus, as non-limiting examples, in a 96 well plate, one waste chamber may be linked to 8 purification chambers, or to 12 purification chambers, such that a separation device would comprise 12 or 8 waste chambers, respectively.

In one embodiment of the invention herein described, the separation device comprises one or more waste chambers that are physically separate from said multiwell plate comprising said purification chambers, and wherein said waste chamber is connected to said purification chamber of said multiwell plate by channels comprised in said lid which guide the supernatant from said purification chamber to said waste chamber under centrifugal force. In a preferred embodiment, said at least one waste chamber is molded to the multiwell plate comprising the purification chambers, forming a separate layer of the separation device. In some embodiments the waste chambers can be mounted along a radius outside the multiwell plate and are connected to the multiwell plate. They rotate along with the multiwell plate, are permanently fixed to the multiwell plates and are aerated by a filter which can hold back liquids and aerosols. In other embodiments, the space between wells in the multiwell plate can be used as a waste chamber. In case the volume of the space between the wells in the multiwell plate is too small, the edge of the plate can be elongated to enlarge the volume. In this case, the space has to be compartmentalized (see FIG. 2). For each row that is processed in parallel, there is one compartment. Each compartment is aerated.

In a further preferred embodiment of the present separation device, said interface comprises a wall between said first and second chamber which is interrupted to allow the supernatant to transfer from said first to said second chamber under centrifugal force. More preferably, the length of the walls between said two chambers is dimensioned such that a gap is present between said walls and said lid, wherein said supernatant can be transferred from said first chamber to said second chamber through said gap under centrifugal force. The term "gap" as used herein relates to an opening present in a surface. In a preferred embodiment, said gap is located in the side wall of a purification and a waste chamber and forms an open connection through which a fluid can pass.

One advantage of the present invention is that a modified lid can be combined with conventional multiwell plates, or that a modified multiwell plate can be combined with a conventional lid to obtain a separation device according to the present invention. Therefore, it is possible to also use already existing components.

In another preferred embodiment of the separation device described hereinbefore, said lid is permanently attached to said vessel. Thus, the lid may be an integral part of the device hereinbefore described.

In a more preferred embodiment of the separation device hereinbefore described, said waste chamber comprises a superabsorber capable of absorbing said supernatant.

The solid phase comprised in the separation device preferably comprises magnetic particles capable of binding nucleic acids. More preferably, said binding of nucleic acids is either generic or specific.

Furthermore, it is advantageous for the present invention that said at least one waste chamber is ventilated.

In one preferred embodiment, the separation device hereinbefore described comprises an upper layer of purification chambers, a lower layer of waste chamber(s) and a space between waste chambers to allow insertion of magnetic pins. One embodiment of the present invention is a separation device as described hereinbefore and movable magnetic pins, wherein multiple magnetic pins can be moved into a position for attracting magnetic particles such that one pin is positioned next to 2 or 4 purification chambers.

In another preferred embodiment, the separation device comprises ring magnets, wherein one ring magnet is positioned underneath one separation chamber.

Further preferred embodiments of the separation device of the present invention are embodiments described hereinafter in relation to a separation method, a lid, a vessel and an analytical system and in the examples.

The present invention also relates to a vessel for holding a liquid comprising an analyte and a solid phase to which said analyte can be bound, comprising
  at least one purification chamber holding said liquid and said solid phase, wherein said analyte is bound to said solid phase within said purification chamber,
  at least one waste chamber to which the liquid can be transferred following binding of the analyte to the solid phase,
wherein a connecting opening is present between said purification chamber and said waste chamber to allow the liquid to transfer from the purification chamber holding the solid phase to said waste chamber when exposed to centrifugal force after said analyte is bound to said solid phase, while the solid phase remains in said purification chamber. In a preferred embodiment, said vessel is a multiwell plate. Generally, the shape of the purification chamber of said microwell plate is conical. In a preferred embodiment, said vessel can be combined with a regular lid as known in the prior art, wherein the interaction between vessel and lid is reversible. In another preferred embodiment, said vessel can be permanently fixed to a lid. In both embodiments, the interface between lid and vessel defines channels that allow the liquid to pass from the purification to the waste chamber, as has been described hereinbefore already in relation to the separation device of the present invention.

The present invention also relates to a lid for connecting at least one purification chamber with at least one waste chamber. Said at least one purification chamber holds a liquid and a solid phase, wherein an analyte is bound to said solid phase within said purification chamber. Said lid forms an interface with said at least one purification chamber and at least one waste chamber to allow said liquid to pass from said at least one purification chamber to said at least one waste chamber after the analyte is bound to the solid phase. Preferably, said interface is a gap or a channel present on the lid, said gap or channel connecting the purification chamber with the waste chamber. The lid of the present invention also comprises openings for inserting a pipette tip to pipette the components necessary for the separation method of the present invention into the purification chambers.

The present invention also relates to a method of separating a liquid from a solid phase comprising the steps of
incubating a liquid sample with a solid phase capable of binding an analyte contained in said liquid sample
separating the liquid from said solid phase after binding of the analyte to the solid phase, wherein said liquid and said solid phase are contained in the separation device as described hereinbefore,
wherein said separating comprises centrifuging said separating device around an axis outside of the separation device holding said liquid to transfer said liquid into one or more waste chambers, wherein said waste chambers are aerated.

In one preferred embodiment, the axis for centrifugation is located outside of the separating device.

Preferably, said separating device is in an upright position during centrifugation. More preferably, said centrifuging is performed with a swing-out rotor or a fixed angle rotor. In one preferred embodiment, the angle between the axis of centrifugation and the side walls of the vessels of said separating device is 1° to 46°. If an upright separation device is centrifuged as described herein, the liquid present in the purification chamber is forced to the wall of the purification chamber opposite of the centrifugation axis. Thereby, the liquid is forced out of the purification chamber through the gaps in the interface between separation and waste chamber, or into fluidic channels. Thus, separation of liquid and solid phase is achieved. The purification chamber commonly have a slightly conical shape. The time required for separation depends on the angle and the speed. As a non-limiting example, with an acceleration of about 10 g, the liquid is accelerated out of the purification chamber within less than 1 sec. The solid phase is immobilized on the side wall of the purification chamber, or, in the case of magnetic particles, the particles can be immobilized on the bottom of the purification chamber by a magnetic field. In this non-limiting example, the angle between the rotation axis and the side walls of the vessels of said separating device has to be at least 6° according to the formula $$a > \arctan(1/n),$$

whereby n is the factor of gravitational acceleration necessary to transfer the liquid completely out of the purification chamber.

In order for the solid phase to remain in the purification chamber while the liquid is transferred into the waste chamber via the lid, the force that is exerted on the solid phase, preferably the magnetic force that is exerted on magnetic particles, has to be greater than the force that the solid phase is exposed to by centrifugal force. This method allows to reduce the void volume after separation by about 2000 fold, compared to conventional separation methods. Additionally, experiments have shown that no particles are lost due to centrifugation. This allows to reduce the number of washing steps and increases the sensitivity and accuracy of analytical procedures which are subsequently performed to determine the amount of analyte. The process described herein makes it clear that during separation, the liquid always moves away from the axis of centrifugation.

As already described hereinbefore for the separation device, the vessel and the lid, the separation of liquid and solid phase occurs by the method hereinbefore described when a lid is mounted onto the vessel comprising purification chambers which interfaces with the purification chambers such that gaps or channels are formed that allow the liquid to transfer from said purification chamber to a waste chamber under conditions hereinbefore described. Further preferred embodiments of device, vessel and lid used in the method of the present invention are as described hereinbefore.

In order for the liquid to pass from the purification chamber to the waste chamber without any resistance, it is necessary for the waste chamber to be aerated. In one preferred embodiment, the waste chamber is aerated by opening, more preferably by a septum that is permeable for gas. Said septum is mounted on said opening of the waste chamber.

In a preferred embodiment, the solid phase of the present method comprises magnetic particles. Thus, the method, in a more preferred embodiment, comprises immobilizing the magnetic particles during centrifugation by applying a magnetic field, most preferably by moving magnetic pins into proximity of the purification chambers to immobilize the magnetic particles.

In a most preferred embodiment, the method of the present invention is automated.

In a preferred embodiment of the method, device and vessel hereinbefore described, said waste chambers comprise a superabsorber capable of immobilizing the liquid. This allows to prevent formation of aerosols which may contaminate the purification chamber during subsequent steps.

The term "superabsorber" as used herein relates to super-absorbent polymers. Such polymers, which are well known in the art, are capable of absorbing liquid to an extent of a multiple of their own mass, preferably up to 1000 fold of their own mass.

Following separation, the analyte comprised in the solid phase is either washed again, solubilized or eluted by adding a liquid to the solid phase. After elution or solubilization, the liquid comprising the purified analyte is then transferred to a reaction vessel for further processing. In one embodiment, the purification chamber is the reaction vessel.

The present invention also relates to a sample preparation system comprising
a centrifuge capable of holding a separation device as described hereinbefore
wherein a separation device as described hereinbefore can be immobilized either horizontally or at an angle between the axis of rotation and the sidewalls of the purification chambers of 1° to 46°,
a separation device as described hereinbefore.

In one preferred embodiment, the angle between the rotation axis and the outer wall of the separation chamber can be modulated during the purification process.

Preferred embodiments are those described hereinbefore for the separation device, the vessel and the lid and the method of the present invention.

In a preferred embodiment, the sample preparation device further comprises a magnet to immobilize the magnetic particles to which an analyte is bound. Preferably, said magnet comprises pins which can be placed between chambers of the separation device. In a more preferred embodiment, the waste chamber of the separation device comprises a superabsorber to absorb the liquid which is separated from the solid phase and transferred from the purification chamber to the waste chamber.

The present invention also relates to an analytical system comprising a sample preparation device hereinbefore described. The analytical system preferably comprises additionally an amplification module. More preferably, it additionally comprises a detection module. In another more preferred embodiment, the amplification module is an amplification and detection module.

Further preferred embodiments are those described hereinbefore for the separation device, the vessel, the lid, the method and the sample preparation system of the present invention.

DESCRIPTION OF THE FIGURES

FIG. 7 shows a multiwell plate in a horizontal position (a) or at an angle (b) according to the present invention.

The present invention is further described hereinafter by non-limiting examples.

EXAMPLES

The following examples and figures are provided to aid the understanding of the present invention, the true scope of which is set forth in the appended claims. It is understood that modifications can be made in the procedures set forth without departing from the spirit of the invention. Some of the examples that follow are theoretical.

Figure 1:
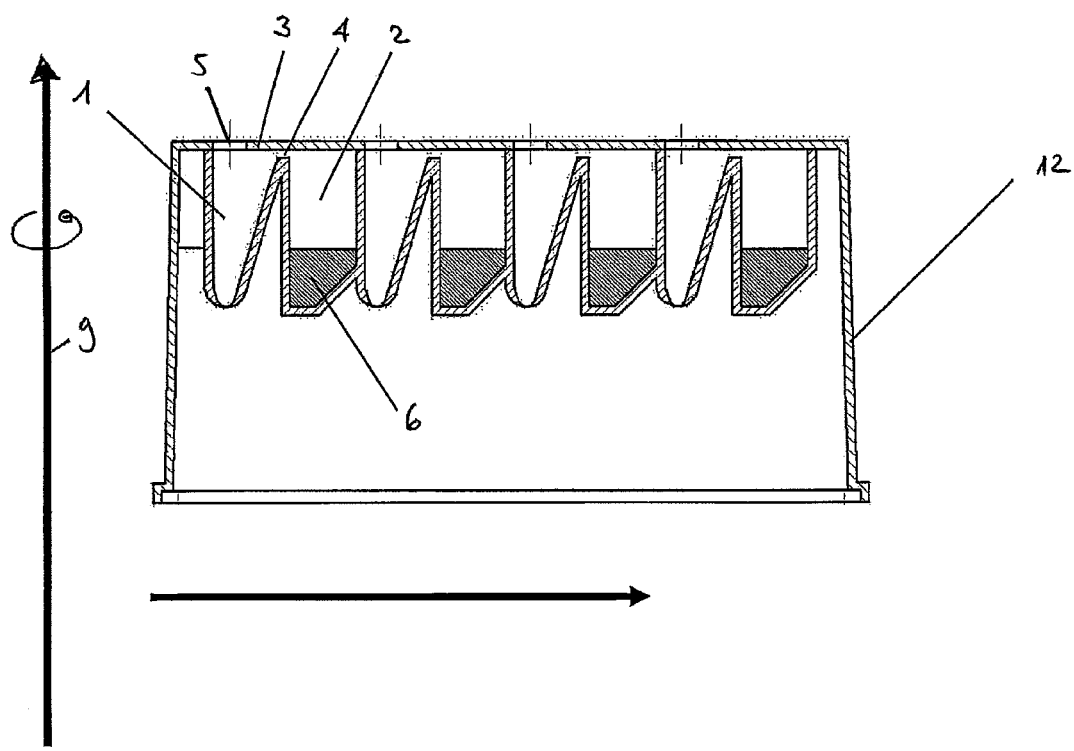
FIG. 1 Sectional view of a multiwell plate (12) with purification chambers (1) and adjacent waste chambers (2). The direction of acceleration is indicated by an arrow. The interface between lid (3) and chambers (1 and 2) comprises a gap (4) between one purification chamber and one waste chamber. A superabsorber (6) is located in the waste chambers. The arrow below the multiwall plate (12) shows the direction of acceleration.
Figure 2:
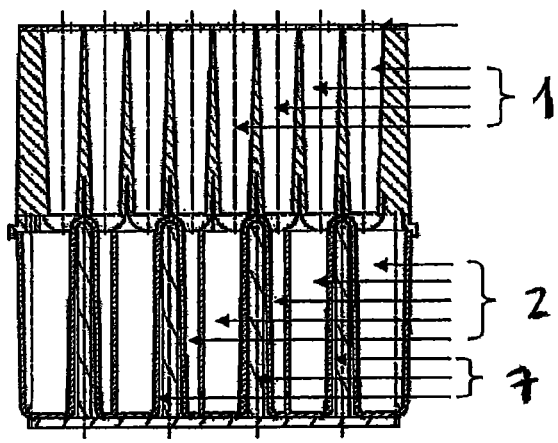
FIG. 2 Sectional view of the narrower side of the multiwell plate.
Figure 3:
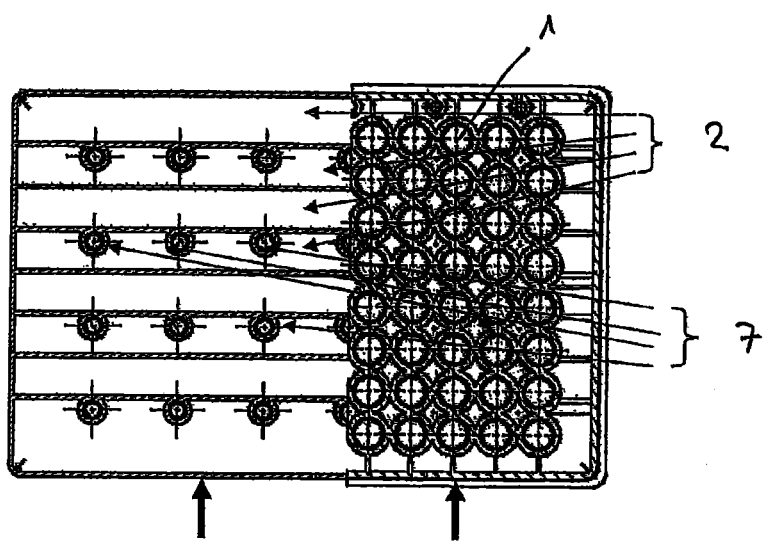
FIG. 3 Top view of the upper and lower parts without lid.

In a 96 well multiwell plate (12) 48 wells are used as purification chambers (1) and 48 wells are used as waste chambers (2). The purification chambers (1) are positioned on the first inside row, closest to the rotor (the rotation axis (9) is shown), and every second row from thereon, and the waste chambers (2) are positioned in every row following a row of purification chambers, as can be seen in FIG. 1. The multiwall plate is covered by a lid (3) and the purification chambers (1) and the waste chambers (2) are connected pairwise by a gap (4). The liquid (5) comprising the analyte, the lysis/binding reagents and the magnetic particles (8) are added to the purification chambers and incubated to allow the analyte to bind to the magnetic particles. Then magnets (7) are positioned next to the multiwell plate such that the magnetic particles (8) are either sequestered on the inside wall (closer to the rotor) or the bottom of the purification chamber. Separation of the liquid (5) from the solid phase (8) is now achieved by centrifugation around an axis (9) which is located outside the multiwell plate. During centrifugation, the plate is fixed either in a horizontal position or in a position with a slight angle (10) to the rotational axis (9) (see FIG. 7 *a*) and *b*)). The rotational movement creates a centrifugal acceleration of several g. The liquid is accelerated to the far wall relative to the rotational axis, but the magnetic particles (8) with the bound analyte do not follow the direction of the acceleration because the magnetic force exerted by the magnetic field on them is stronger than the centrifugal force. Thus, the magnetic particles (8) are held in the purification chambers while the liquid is accelerated out of the separation (1) into the waste chambers (2).

The multiwell plate (12) is designed such that two neighboring wells always form one unit: a conical purification chamber (1) and a waste chamber (2) which may comprise a superabsorber (6). To permit the two wells of a unit to perform as a unit, the multiwell plate (12) is combined with a lid (3) which comprises as many openings (15) as there are units in the multiwell plate, i.e. 48 openings. The two wells of the unit are connected fluidically by gaps (4) between lid and multiwell plate. The gap (4) in the interface between the purification and the waste chamber are formed such that the unit is aerated during transport of liquid from one chamber to the other such that no counter pressure is exerted on the liquid. When the liquid is completely transferred to the waste chamber (2), and the rotor with the MWP on it is stopped and a washing buffer can be added to the solid phases in the purification chamber, and the whole process can be repeated.

FIG. 7 shows an example of a multiwall plate either in a horizontal position (FIG. 7 *a*)) or at an angle (10) (FIG. 7 *b*)), compared to the axis of rotation (9). The lid (3) comprises openings (15) for pipetting, and the purification chamber (1) and waste chamber (2) are connected by a gap (4) through which the liquid (5) to be removed can move from the purification chamber (1) to the waste chamber (2). During centrifugation, the liquid moves up the side wall (23) of the purification chamber (1), while the magnetic particles (8) are kept at the lower side wall (22) of the purification chamber (1) proximal to the axis of rotation.

Example 2

In this example, 96 samples are being purified in parallel in 96 wells of a multiwell plate. Each well, therefore, defines a purification chamber. In the case of the solid phase being magnetic particles, 24 magnets are required wherein each magnet is moved into proximity of 4 wells from below the multiwell plate. In another embodiment, one magnet is moved into proximity of one well, in this case, 96 magnets are used.

Figure 4:
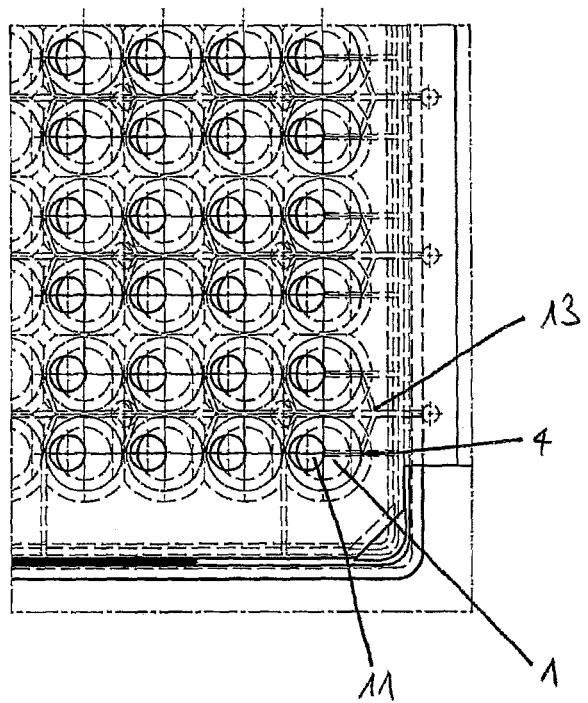
FIG. 4 shows a detailed view of a lid in an embodiment in which the waste chamber is located on the outside of the multiwell plate. The channels for the supernatant lead towards the outside in a fishbone arrangement and the openings for pipetting are open, but can be closed by a lid.

Two possible embodiments exist for purifying 96 samples in parallel: In one embodiment, the supernatant is removed according to the invention via channels mounted between the wells and the lid, whereby the channels are arranged in a fishbone manner (see FIG. 4). All main channels in this arrangement lead into one waste chamber which is located outside of the multiwell plate, wherein outside means at the far side from the axis of rotation. The waste chamber has one or more openings that are leading towards the inside and are aerated by a filter (e.g. a Porex filter).

In a second embodiment, the waste chambers are located underneath the multiwell plate. As an example, if 8 or 12 wells in one row are handled in parallel, a waste chamber per row of 8 or 12 wells is located underneath the multiwell plate.

Example 3

In this embodiment, the analyte is not bound to magnetic particles but to a solid phase which is sequestered based on density. Following binding of the analyte to the solid phase, the solid phase is sequestered by centrifugation in a swing out mode at high acceleration. After sequestration of the solid phase, the centrifuge is stopped. The multiwell plate is then arrested in a horizontal position and centrifuged briefly at a low acceleration. The supernatant is, thus, removed via the lid as described in the previous examples.

Example 4

By the following method, a multitude of samples can be processed simultaneously. The method is particularly useful for non-magnetic particles. There are always two wells of a multiwell plate which form a unit. The biological sample, reagents and particles are incubated in a first well (purification chamber). The plate is centrifuged to separate particles from supernatant. The rotor is swinging out the plate such that the particles are sequestered at the bottom of the wells. The rotor can now be fixed in a horizontal position or at a slight angle. The exact position depends on whether a standard plate is used, or a plate specifically designed for the separation process of the present invention. The rotor now starts to rotate at an acceleration of typically 8 to 10 g. The solution travels up the side wall to a gap located on the outside of the purification chamber (relative to the rotor axis) which connects the purification chamber and the waste chamber. The supernatant flows into the waste chamber and is now separated from the solid phase which is retained in the purification chamber. In the waste chamber, a superabsorber can be located to prevent carry-over of aerosols.

In a second step, a washing buffer is added to the solid phase and the particles are resuspended, e.g. by pipetting up and down, by ultrasound or another method. When an equilibrium is established in the washing solution, the purification process described above is repeated once or twice until the particles are purified. Then the analyte can be eluted from the particles.

Example 5

Figure 5:
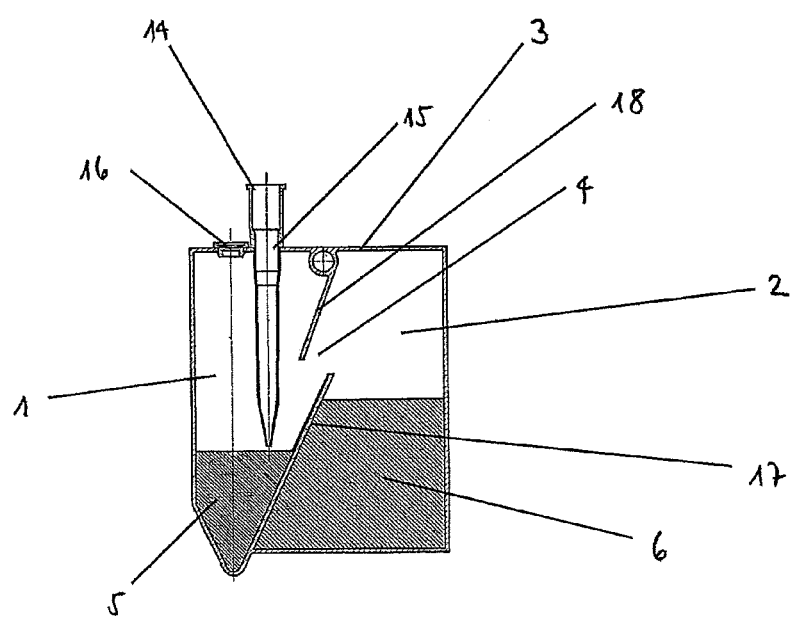
FIG. 5 (*a* to *c*) shows a schematic presentation of the separation method using single purification cassettes.
Figure 5:
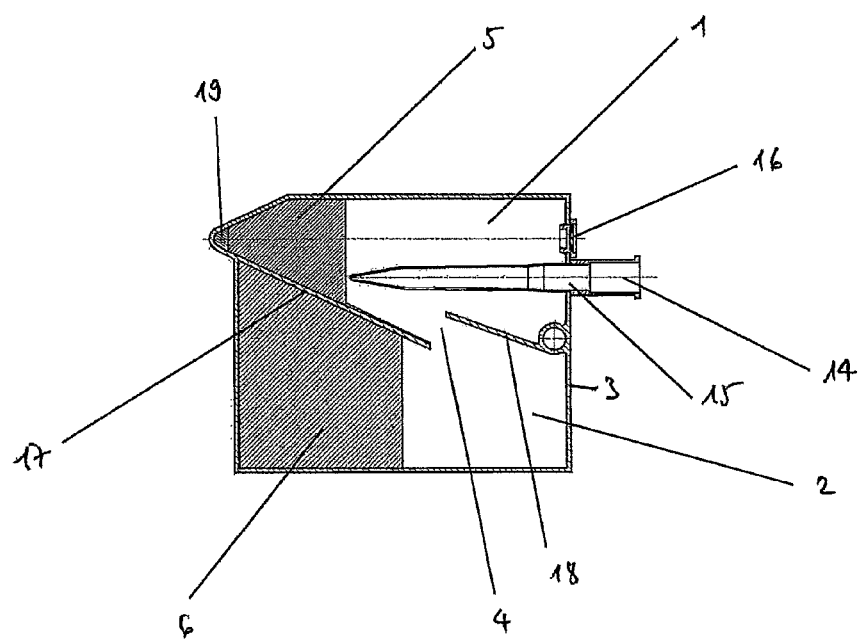
Figure 6:
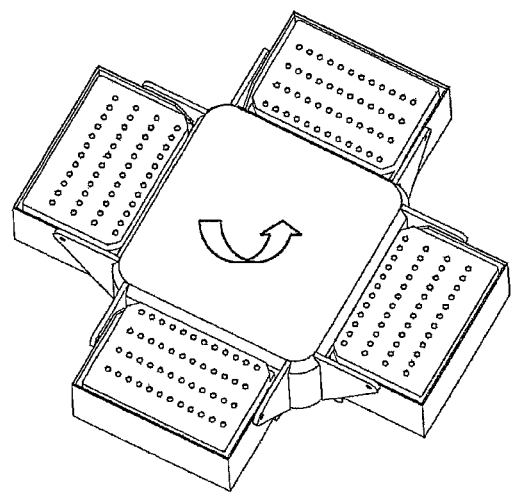
FIG. 6 shows a swing-out rotor for multiwell plate, which can swing out for sequestration of the solid phase and be locked for separating the supernatant via the lid.

The method is not limited to multiwell plates but can also be used for single cassettes as shown in FIG. 5. The cassette comprises one purification chamber (1) with a conical form (20) and a second waste chamber (2) which comprises a superabsorber (6). The two chambers are connected by a gap (4). The gap can be formed by an opening between two sidewall portions (17, 18) which are located between the purification chamber (1) and the waste chamber (2). The cassette is closed on the top (the lid) (3) and has one or two openings (15,16) above the purification chamber which can be closed by a septum. These openings can receive a pipette tip (14, 21) to pipette sample, reagents and solutions into the purification chamber. Solutions that are to be separated from a solid phase (19) in the purification chamber can be removed by centrifugation, typically by 8-19 g. This reduces rest volume of liquid between the particles and makes the purification process more efficient. In a preferred embodiment, the separation can be achieved by centrifugation of the chamber fixed in a horizontal position (as in FIGS. 5 (a) and (c)) or by fixing the chamber in a vertical position (FIG. 5 b)) and by allowing the liquid to drain into the waste chamber (2) without centrifugation.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A separation device for separating a supernatant from a solid phase, comprising
 a multiwell plate for holding one or more liquids comprising one or more analytes and a solid phase to which said analyte can be bound, said multiwell plate comprising
  at least two purification chambers holding said liquid and said solid phase, wherein one or more of said analytes are bound to said solid phase within said purification chambers, said purification chambers not fluidically connected to each other or any other chamber in an opposite direction of said liquid's flow direction,
  at least one waste chamber to which the liquid can be transferred following binding of the analyte to the solid phase, said at least one waste chamber being fluidically connected only to one of said at least two purification chambers or to more than one of said at least two purification chambers without being further fluidically connected to any other chamber in said liquid's flow direction, and
  a lid covering said multiwell plate,
 wherein the interface between said multiwell plate and said lid is a gap in a side wall of the purification chambers, or a gap or a channel present on the lid, said gap in the side wall, or said gap or said channel present on the lid, connecting the purification chambers with the waste chamber to allow the liquid to transfer from the purification chambers holding the solid phase to said waste chamber when exposed to centrifugal force after said one or more analyte is bound to said solid phase, while the solid phase remains in said purification chambers, wherein said side wall of the purification chambers comprises an inclined surface toward the waste chamber.

2. The separation device according to claim 1, wherein said waste chamber comprises a superabsorber capable of absorbing said supernatant.

3. The separation device according to claim 1, wherein said separation device has less waste chambers than purification chambers.

4. The separation device according claim 1, wherein said waste chamber is physically separate from said multiwell plate comprising said purification chambers, and wherein said waste chamber is connected to said purification chambers of said multiwell plate by channels comprised in said lid which guide the supernatant from said purification chambers to said waste chamber under centrifugal force.

5. The separation device according to claim 1, wherein said interface comprises a wall between said purification chambers and said waste chamber which is interrupted to allow the supernatant to transfer from said purification chambers to said waste chamber under centrifugal force.

6. The separation device according to claim 1, wherein the length of the wall between said purification chambers and said waste chamber is dimensioned such that a gap is present between said wall and said lid, wherein said supernatant can be transferred from said purification chambers to said waste chamber through said gap under centrifugal force.

7. The separation device according to claim 1, wherein said lid is permanently attached to said vessel.

8. The separation device according to claim 1, wherein said at least one waste chamber is ventilated.

9. A method of separating a liquid from a solid phase comprising the steps of
   incubating a liquid sample with a solid phase capable of binding an analyte contained in said liquid sample
   separating the liquid from said solid phase after binding of the analyte to the solid phase, wherein said liquid and said solid phase are contained in the separation device according to claim 1,
   wherein said separating comprises centrifuging around an axis outside of the separation device, said separating device holding said liquid to transfer said liquid into one or more waste chambers, wherein said waste chambers are aerated.

10. The method of claim 9, wherein the angle between the axis of centrifugation and the side walls of the purification chambers and the waste chamber of said separating device is 1° to 46°.

11. A sample preparation system comprising
   a centrifuge comprising a rotor capable of holding a separation device according to claim 1,
   wherein a separation device according to claim 1 can be immobilized either horizontally or at an angle between the axis of rotation and the sidewalls of the purification chambers of 1° to 46°,
   a separation device according to claim 1.

12. The separation device according to claim 1, wherein said solid phase comprises magnetic particles.

13. The method according to claim 9, wherein said solid phase comprises magnetic particles.

14. The method of claim 13, further comprising immobilizing the magnetic particles during centrifugation by applying a magnetic field.

* * * * *